United States Patent
Karow et al.

(10) Patent No.: US 6,626,172 B1
(45) Date of Patent: Sep. 30, 2003

(54) DEVICE FOR INSERTION INTO THE HUMAN NOSE

(76) Inventors: Eva-Maria Karow, Brotzenmuhle 1, D-65604 Elz (DE); Jonathan Stirmann, Amselweg 8, D-55546, Frei-Laubersheim (DE); Peter Rickauer, Bugelrainstrabe 4, 83233 Bernau (DE); Dirk Schneider, Mowenweg 7, 56170 Bendorf (DE); Bernhard Kramer, Breitenstrabe 4, 83250 Marquartstein (DE); Olaf Michel, c/o Oberlander, Vorgebirgsstrabe 263, 50696 Koln (DE)

( * ) Notice: Subject to any disclaimer, the term of this patent is extended or adjusted under 35 U.S.C. 154(b) by 0 days.

(21) Appl. No.: 09/674,385

(22) PCT Filed: Apr. 30, 1999

(86) PCT No.: PCT/DE99/01332

§ 371 (c)(1),
(2), (4) Date: Jan. 16, 2001

(87) PCT Pub. No.: WO99/55404

PCT Pub. Date: Nov. 4, 1999

(30) Foreign Application Priority Data

Apr. 30, 1998 (DE) .......................... 198 32 205
Apr. 30, 1998 (DE) ...................... 298 07 851 U

(51) Int. Cl.⁷ .............................................. A61M 15/00
(52) U.S. Cl. ........................... 128/200.24; 128/206.11; 128/848; 606/199; 606/196

(58) Field of Search .................. 128/207.18, 200.24, 128/204.13, 206.11, 848, 857, 858, 912; 602/12, 13, 14, 15, 16, 17, 60, 61, 74, 46, 47; 606/191, 196, 199, 201, 204.15, 204.45

(56) References Cited

U.S. PATENT DOCUMENTS

| | | | |
|---|---|---|---|
| 1,839,606 A | | 1/1932 | Simmons |
| 3,935,859 A | | 2/1976 | Doyle |
| 4,201,217 A | * | 5/1980 | Slater .................. 606/199 |
| 5,479,944 A | * | 1/1996 | Petruson .............. 128/858 |
| RE35,408 E | * | 12/1996 | Petruson .............. 128/858 |
| 5,855,908 A | * | 1/1999 | Stanley et al. ....... 424/439 |

FOREIGN PATENT DOCUMENTS

| | | |
|---|---|---|
| EP | 0 780 137 | 6/1997 |
| WO | 88 03788 | 6/1988 |
| WO | 96 29034 | 9/1996 |

* cited by examiner

*Primary Examiner*—Weilun Lo
*Assistant Examiner*—Michael Mendoza
(74) *Attorney, Agent, or Firm*—Frommer Lawrence & Haug

(57) ABSTRACT

A device for insertion into the human nose, characterised by having at least one elastically deformable plate-like base element with an inner side and an outer side and with a substantially rectangular shape, said element being substantially flat or slightly arched in its unstressed condition.

16 Claims, 2 Drawing Sheets

DEVICE FOR INSERTION INTO THE HUMAN NOSE

FIELD OF THE INVENTION

The invention relates to a device for insertion into the human nose which is particularly suitable for the application of pharmaceutical active agents, for the exposure of diagnostic agents in the nose and for improving nasal breathing.

BACKGROUND FOR IMPROVING NASAL BREATHING

Obstructed nasal breathing can have a wide variety of causes. Congenital or acquired deformities in the osseous or cartilaginous nose structure, for example, can be the cause, as can chronic inflammatory or degenerative changes to the tissue.

The respiratory flow through the human body begins when air flows through the vestibule of the nose, or vestibulum nasi. Deformities in the nasal cartilage and inadequate elasticity in the structures of the connective tissue can lead to a constriction of the vestibulum nasi. Furthermore, during inhalation, it can happen that the wings of the nose are drawn in, leading to restricted nasal breathing. Since degenerative changes to the structures of the connective tissue are often responsible for the latter, this phenomenon occurs more often at a more advanced age and is not infrequently responsible for disturbing snoring noises.

In the case of the application for improving nasal breathing, the effect is to optimise the lumen situation in the region of the vestibulum nasi. For this purpose, the device, which may be shaped like a butterfly, is placed in the region of the vestibulum nasi in such a way that it dilates the nostrils or prevents the wings of the nose from being drawn in during inhalation and thus maintains or enlarges the internal diameter of the vestibulum nasi.

BACKGROUND FOR THE APPLICATION OF PHARMACEUTICAL ACTIVE AGENTS

The nasal mucous membrane has good absorbent properties and is therefore in principle a good alternative route for applying pharmaceutical agents. Experiments have been conducted in applying both vaccines and various pharmaceutical agents via the nasal mucous membrane. It became apparent that problems in this connection were posed by the natural clearance system in the main nasal cavity. This system is capable of clearing substances applied to the nasal mucous membrane within an average of 10 minutes, i.e. transporting them towards the pharynx, from where the substances are then either expectorated or swallowed, which prevents adequate absorption.

Conventionally, in order to apply pharmaceutical agents in the main nasal cavity, presentations such as solutions or ointments are chosen. These presentations have the great disadvantage that they apply the pharmaceutical active agent in a kind of bolus. The consequence of this is firstly that the bolus is transported away quite quickly by the normal clearance behaviour of the nasal mucous membrane. Secondly, the massive short-term burden on the nasal mucous membrane stimulates the cleansing performance of the clearance apparatus, so that the rate of removal is increased still further. The consequence of this is that the pharmaceutical agents applied are often eliminated more quickly by mucociliary clearance than they can be absorbed.

BACKGROUND FOR THE APPLICATION OF DIAGNOSTIC AGENTS

Because of its proximity to and constant contact with the environment, the nasal mucous membrane is to a particularly high degree exposed to external irritations which not infrequently lead to hypersensitivity reactions and can even trigger pronounced allergies. Identifying the agent triggering the allergy is of great importance here, since it is only in this way that the causes can be treated in the form of avoidance of allergens or hyposensitisation. So far, intracutaneous tests or prick tests have been used for this purpose. These are in vivo test methods which test the body's reaction to specific antigens in the skin of the lower arm or back. Their great disadvantage is that these test methods do not permit any statement to be made about the clinical relevance of their results because they do not provide any information concerning the acute processes taking place in the nose. These studies are therefore often used for screening purposes before subsequently carrying out a nasal provocation in a more targeted way. These studies are very sensitive and specific, but have the disadvantage that they can lead to powerful local reactions in the patient and that it is not possible to test a variety of allergens one immediately after the other.

In the context of a rhinitis allergica, for example, specific antibodies are raised against the antigen, the process occurring principally locally, at least at the beginning of the condition. Antibodies can therefore be found particularly in the nasal mucous membrane and in the nasal secretion.

The problem on which the invention is based consists in providing a device for insertion into the human nose which is suitable firstly for improving nasal breathing, i.e. which offers benefits in terms of its adaptability to different dimensions of the nasal vestibule and which also, where possible, creates a greater cross-sectional area for the flow of respiratory air; secondly, the device also forms a support or frame for therapeutic systems by which pharmaceutical active agents can be applied to the nasal mucous membrane in order for said agents then to be released in a delayed manner, or it is provided with diagnostic agents in order to be able to carry out different diagnostic reactions or tests in a simple way.

SUMMARY OF THE INVENTION

In accordance with the invention, this problem is solved by means of a device for insertion into the human nose which is characterised by having at least one elastically deformable plate-like base element with an inner side and an outer side and with a substantially rectangular shape, said element being substantially flat or slightly arched in its unstressed condition.

The base element can be designed in a slight butterfly shape, with two wings disposed symmetrically relative to a central line.

Laterally and/or at the top, the base element may be bevelled. The base element may be thicker in its central portion.

Provision can be made for the base element to possess a thread-like or rod-like extension for insertion and removal purposes.

The device can be made of a material suitable for remaining in the body cavity for a lengthy period, such as silicone rubber.

In a preferred embodiment, it is envisaged that the base element may be provided on the inner side and/or on the outer side with at least one pharmaceutical agent to be applied and/or at least one diagnostic agent.

In one embodiment of the device, it is envisaged that recesses may be provided on the inner side and/or on the outer side.

It is envisaged that platelets or sponges based on cellulose may be provided on the inner side and/or the outer side, or optionally in the recesses, as substrates for pharmaceutical agents and/or diagnostic agents. Alternatively, transmucosal and/or nasal therapeutic reservoir or matrix systems may be disposed inner side and/or outer side, or optionally in the recesses, as substrates for pharmaceutical agents and/or diagnostic agents.

In a preferred embodiment, it is envisaged that a second base element can be connected to the first base element via connecting means to form a single unit.

The invention also relates to the use of the device according to the invention for improving nasal breathing and/or for applying pharmaceutical agents and/or for exposing diagnostic agents in the nose.

When the invention is used for applying pharmaceutical agents, the latter can be applied to the device in a carrier layer or matrix on one or both sides, and their release can be adjusted as required either directly from the matrix or through a diffusion layer (membrane) disposed above it. In this way, it is possible to ensure that the pharmaceutical agents are released steadily in small doses, which increases their overall absorption rate. In addition, their use over any desired period makes it possible to achieve an even level of effective action over a defined period.

When the invention is used for exposing diagnostic agents, the corresponding substances, which are firmly bound to the device of the invention and can communicate with the environment, can be placed in the nasal vestibule for a period of approx. 20–30 minutes, for example. When the patient is suffering from an allergy, for example, an antigen positioned in this way can produce an antigen-antibody reaction which can later be detected by means of enzymatic or radiological immunoassays. With this method, it is thus possible to make a statement about the situation in the nasal mucous membrane at the time in question, without subjecting the patient to invasive measures or measures harmful to health. Furthermore, the method makes it possible to test various allergens simultaneously, because approx. 10 or more antigens can be applied to the device of the invention, which facilitates rapid diagnosis in a way that can be performed anywhere, including during everyday work in a doctor's surgery. It goes without saying that the invention is not, however, restricted to the exposure of allergens; all diagnostic agents which can reasonably be used in the nasal region can be used.

BRIEF DESCRIPTION OF THE DRAWING

Further advantages and features of the invention may be learned from the following description of preferred embodiments, reference being made to a drawing, in which.

DESCRIPTION OF PREFERRED EMBODIMENTS

Figure 3A:
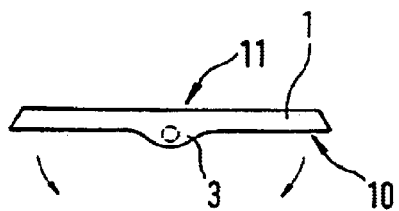
FIGS. 3(a) to (c) show views from above in three different bending positions.
Figure 3B:
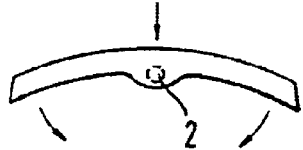
Figure 3C:
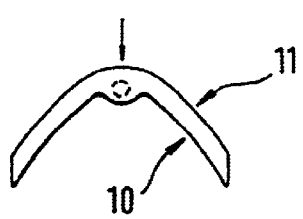
Figure 4:
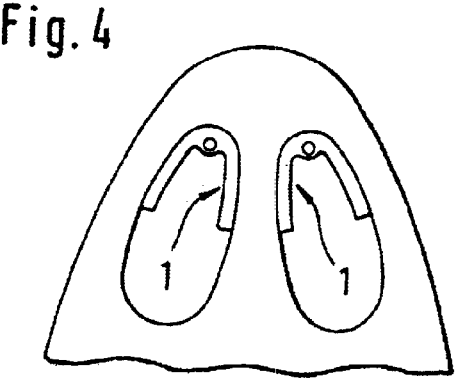
FIG. 4 shows the immobilisation position of the device in the nasal vestibule.
Figure 8:
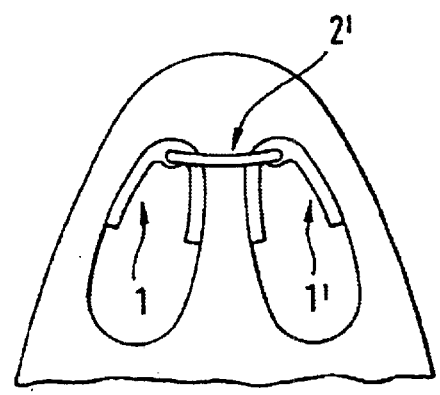
FIG. 8 shows the device according to FIG. 7 in the immobilised position in the nasal vestibule.
Figure 7:
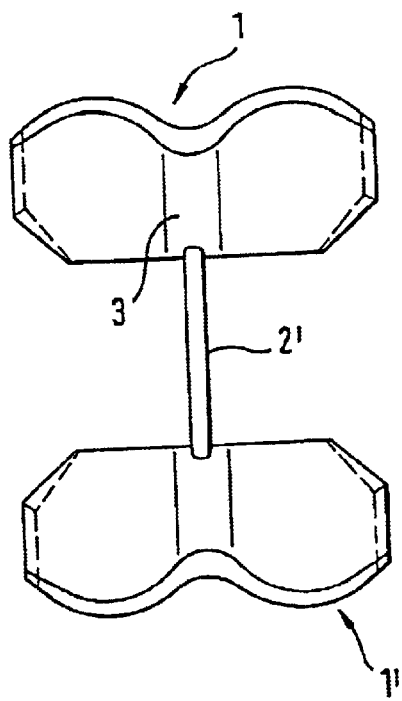
FIG. 7 shows a further embodiment of the device of the invention.

FIGS. 1 to 6 show the structure of the device of the invention and the way in which it works, wherein it is possible for the device to be used singly, i.e. separately for the left or right nostril in each case, as is shown in FIG. 4, the two devices being identical, or as a single unit comprising two base elements 1 and 1', in which the base elements of the two devices are joined together via a thread-like connecting means 2', for example (FIGS. 7, 8).

Figure 1:
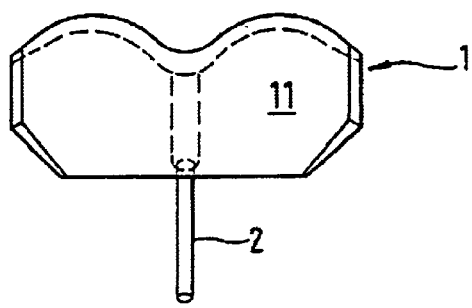
FIG. 1 shows a plan view of a first embodiment of the device of the invention seen from the front.
Figure 2:
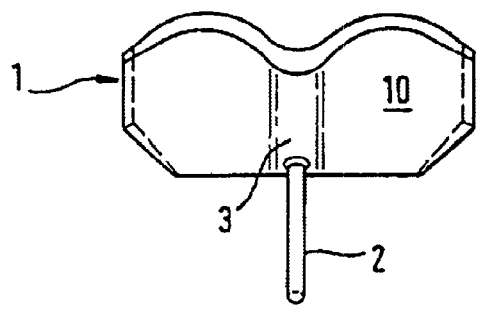
FIG. 2 shows a plan view of the device of the invention according to FIG. 1 seen from the rear.

FIGS. 1 and 2 show a (flat) plan view from the front and rear of the device respectively, the device being substantially plate-like, the view from above according to FIG. 3(a) showing the substantially constant thickness of the device. The plate-like base element 1 is substantially rectangular or, in a preferred embodiment, shaped slightly like a butterfly, as is shown by FIGS. 1 and 2, and is adapted in shape and size to the conditions of the nasal vestibule (vestibulum nasi) in such a way that it can be firmly positioned therein. Base element 1, which is essentially flat or slightly arched in an unstressed state and which thus, because of its elastic deformability, possesses an expanding force that is normally sufficient for it to fit well, is firmly positioned simply by inserting it into the nasal vestibule (FIG. 4) and, in principle, can remain there for any desired length of time. The thickness and/or size (width and length) of the base element are adapted to the individual requirements of the user by providing graduated dimensions for example. In order to improve the positioning, it is (also) possible to provide thicker portions on the lateral edges of the device, corresponding to the central thickening 3.

Secure immobilisation is achieved not only by the specific construction (shape of the wings, bevelling towards the rear, gable shape, etc.), which is adapted to the anatomical conditions, but above all also by the expanding force obtained through the structure or by means of a suitable choice of materials. The device of the invention thus rests firmly against the mucous membrane of the nasal vestibule and is in direct contact with the latter via the outer surface 11 of the base element, whereas the inner surface 10 of the base element is in contact with the flow of respiratory air.

Figure 9:
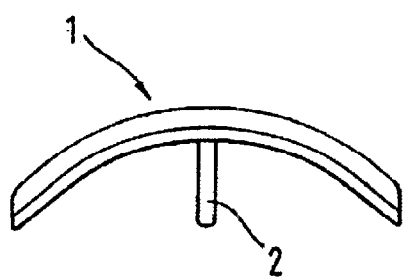
FIG. 9 shows a variant of the device of the invention.

In order to facilitate the insertion and removal of the device, the plate-shaped base body 1 is provided with a thread-like or rod-like extension 2 which extends from the lower longitudinal edge of the base element. In addition, the plate-shaped base element is provided with a thickening 3 in its central portion in order to vary, or to adjust and improve the positioning and the expanding force. Alternatively, it is possible to dispense with such a thickening (FIG. 9) if the expanding force for optimum positioning or attachment is provided by the choice of material or the coating with a mucosal and/or nasal therapeutic system containing the pharmaceutical active agent or with diagnostic agents.

FIGS. 3(a) to (c) show various stages in the deformation of the device of the invention for the purpose of insertion into the nasal vestibule, the latter (final) condition being shown in FIG. 4. The device is inserted with its medial portion pointing towards the tip of the nose, the wings touching the lateral and medial nasal wall. No external braces, adhesives or the like are needed.

The device of the invention is preferably made from materials which may temporarily, i.e. for up to about a month (or even longer), remain in a body cavity such as the nose and which will not dissolve or produce any undesired side effects during that time, silicone rubber being an example of such a material.

The pharmaceutical active agent(s) to be applied can be embedded in a matrix which is attached to the inner and/or outer side of the base element. All the standard matrix formers for medical use are conceivable for the matrix, such as polyacrylate, silicone. silicone oil, polyisobutylene, rubber, rubber-like synthetic homopolymers. copolymers or block polymers, butyl rubber, styrene/isoprene copolymers, polyurethanes, ethylene copolymers, polysiloxane or styrene copolymers.

The transmucosal and/or nasal therapeutic system for the application of pharmaceutical agents, which is attached to the device of the invention, can consist solely of the matrix described above containing the pharmaceutical active agent (s). Delayed release of the pharmaceutical active agents is achieved directly from the structure of the matrix in the process.

Figure 5:
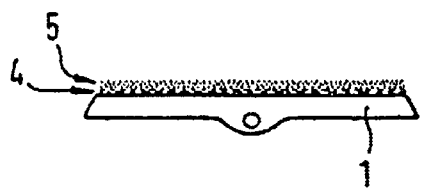
FIG. 5 shows the application of a pharmaceutical agent and a diffusion layer (membrane) on the device of the invention.
Figure 6:
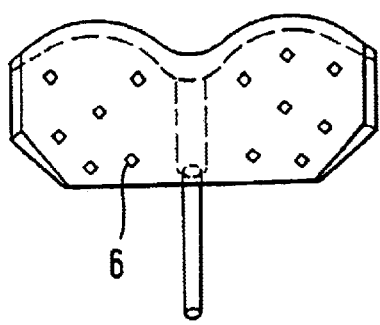
FIG. 6 shows the application of diagnostic agents/pharmaceutical agents on the device of the invention.

Another possibility (as shown in FIG. 5) consists in applying a diffusion layer (5) over the layer 4 (which can be a matrix as described above) containing the pharmaceutical active agent(s), said diffusion layer (5) also being known as a membrane, in order to control the release of the pharmaceutical active agents. A difflusion layer of this kind can consist, for example, of inert polymers, especially on the basis of polypropylene, polyvinyl acetate, polyamide, ethylene vinyl acetate or silicone.

Pharmaceutical active agents that might be used include, inter alia, hormones (calcitonin, insulin, heparin) and vaccines (active immunisation). Other examples are vasoconstrictors or NO synthase inhibitors, nitroglycerine, essential oils, analgesics, e.g. morphium and its derivatives, migraine agents, e.g. triptans (sumatriptan, rizatriptan benzoate, naratriptan) or also ergotamine derivatives, and scopolamin.

Unlike pharmaceutical active agents. diagnostic agents remain firmly bound on or in the device and are analysed at the end of the examination period (e.g. 30 minutes).

Examples of diagnostics are allergens, such as mould allergens, mite dropping allergens and all kinds of pollen allergens and binding proteins for cytokines and cell labels.

In order to facilitate the insertion and removal of the device, the plate-like base element is normally provided with a thread-like or rod-like extension which extends from a longitudinal edge of the base element. A further possibility consists in joining two base elements together, e.g. via said extension. A connection of this kind could for example take the form of a thin thread or cord, made of silicone rubber for example. This allows the simultaneous application of two base elements, i.e. one for each nostril, without the risk of aspiration or conveyance into the rear portion of the main paranasal cavity. Apart from that, insertion and removal is further facilitated. FIGS. 7 and 8 illustrate this embodiment.

In addition, it is possible for recesses 6 to be provided on the inner side 10 and/or outer side 11 of the device (FIG. 6), in which it is possible to insert platelets or sponges on a cellulose basis as substrates for chemically bound allergens, for example. Alternatively, such platelets on a cellulose basis containing allergens can also be attached directly to the device without the need for the presence of a recess. It is also possible to insert into the recesses conventional transmucosal and/or nasal therapeutic reservoir or matrix systems (with or without a difflusion layer), which contain one or more pharmaceutical active agents. Pharmaceutical active agents which are intended to act transmucosally can be integrated on the side facing the nasal mucous membrane (outer side 11). Agents acting by inhalation, such as essential oils, can be applied to the side facing away from the mucous membrane, or facing the flow of respiratory air (inner side 10).

The invention thus provides the benefits (1) of offering good, easy and reliable positioning in the nasal vestibule and similar ease of removal, (2) of being in even and good contact with the mucous membrane of the nasal vestibule and, (3) of being designed such as to be infinitely variable with regard to the duration of application.

The features of the invention disclosed in the above description, in the drawings and in the claims can be essential both individually and in any combination in implementing the invention in its various embodiments.

What is claimed is:

1. A device for insertion into the human nose having an elastically deformable plate-shaped base element which is substantially flat or slightly arched in its unstressed condition before insertion into the nose wherein said base element is deformable into a u-shape along a central line and, when it is deformed into a u-shape, said device when inserted into a nose is applied partly against the nasal septum and partly against the nasal outer wall so that it exerts an expanding force between the nasal septum and the nasal outer wall.

2. A device as claimed in claim 1 wherein said base element is formed to have a butterfly shape with two wings disposed symmetrically relative to a central line.

3. A device as claimed in claims 1 or 2 wherein said base element is beveled at its side and/or at its top.

4. A device as claimed in claims 1 or 2 wherein said base element has a thicker central portion.

5. A device as claimed in claims 1 or 2 wherein said base element includes a thread-like extension to facilitate insertion and removal of said base element from a nose.

6. A device as claimed in claims 1 or 2 wherein said base element includes a rod-like extension to facilitate insertion and removal of said base element from a nose.

7. A device as claimed in claims 1 or 2 wherein said device comprises a material which is suitable for remaining in a body cavity for a lengthy period of time.

8. A device as claimed in claims 1 or 2 wherein the device consists of silicone rubber.

9. A device as claimed in claims 1 or 2 wherein said base element is provided with at least one pharmaceutical agent to be applied and at least one diagnostic agent.

10. A device as claimed in claims 1 or 2 wherein said base element is provided with at least one pharmaceutical agent to be applied or at least one diagnostic agent.

11. A device as claimed in claims 1 or 2 wherein said base element includes a plurality of recesses therein.

12. A device as claimed in claims 1 or 2 wherein said base element includes a plurality of recesses therein and wherein platelets or cellulose sponges are provided in said recesses as substrates for pharmaceutical and/or diagnostic agents.

13. A device as claimed in claims 1 or 2 wherein said base element includes a plurality of recesses therein and wherein transmucosal and/or nasal therapeutic reservoirs are provided in said recesses as substrates for pharmaceutical and/or diagnostic agents.

14. A device as claimed in claims 1 or 2 wherein a second base element is provided connected to said first base element to form a single unit.

15. A method for improving nasal breathing and/or for applying pharmaceutical or diagnostic agents in the nose comprising inserting a substantially flat or slightly arched plate-shaped base element into the nose which deforms into a u-shaped member applied partly against the nasal septum and the applied partly against the nasal outer wall and impregnating said base element with a pharmaceutical and/or diagnostic agent.

16. The method according to claim 15 wherein said base material includes a plurality of recesses and said pharmaceutical and/or diagnostic agent is contained within said recesses.

\* \* \* \* \*